United States Patent [19]
Tobia

[11] Patent Number: 5,315,989
[45] Date of Patent: May 31, 1994

[54] MEDICAL VENTILATOR

[75] Inventor: Ronald L. Tobia, Aberdeen, N.J.

[73] Assignee: BOC Health Care, Inc., New Providence, N.J.

[21] Appl. No.: 803,927

[22] Filed: Dec. 9, 1991

[51] Int. Cl.⁵ .......................................... A61M 16/00
[52] U.S. Cl. ............................ 128/204.28; 128/205.24
[58] Field of Search ..................... 128/204.28, 204.18, 128/204.21, 204.26, 205.24

[56] References Cited

U.S. PATENT DOCUMENTS

| | | | |
|---|---|---|---|
| 3,976,064 | 8/1976 | Wood | 128/204.28 X |
| 4,527,557 | 7/1985 | DeVries et al. | 128/204.23 |
| 4,838,257 | 6/1989 | Hatch | 128/204.18 |
| 5,040,529 | 8/1991 | Zalkin | 128/204.18 |

FOREIGN PATENT DOCUMENTS

| | | | |
|---|---|---|---|
| 46570 | 3/1982 | European Pat. Off. | 128/204.22 |
| 0282675 | 9/1988 | European Pat. Off. | |
| 491969 | 7/1992 | European Pat. Off. | 128/204.22 |
| 2715003 | 10/1978 | Fed. Rep. of Germany | 128/204.28 |
| 3712389 | 10/1988 | Fed. Rep. of Germany | 128/204.28 |
| 85/00983 | 3/1985 | World Int. Prop. O. | 128/204.22 |

Primary Examiner—Edgar S. Burr
Assistant Examiner—Eric P. Raciti
Attorney, Agent, or Firm—Roger M. Rathbun; Larry R. Cassett

[57] ABSTRACT

A medical ventilator is provided which continuously controls both inspiratory and expiratory flow and pressure, including positive end expiratory pressure (PEEP), through control of a single inspiratory flow-control valve. This valve controls inspiratory flow and pressure and, during expiration, controls expiratory flow and pressure by controlling the pressure within the back chamber of an expiratory diaphragm or balloon-type valve. Feedback signals preferably are provided to the valve's controller to provide inspiratory closed-loop flow control and continuous inspiratory and expiratory closed-loop pressure control.

7 Claims, 3 Drawing Sheets

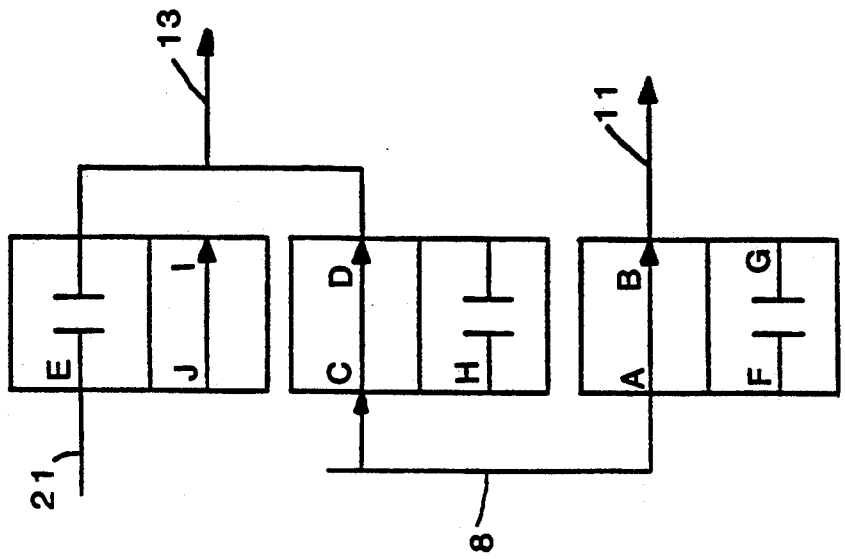
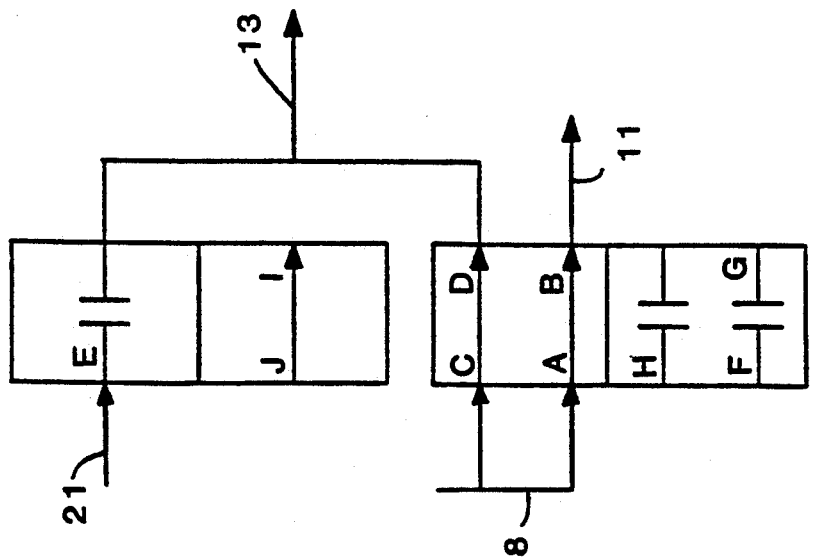

MEDICAL VENTILATOR

BACKGROUND OF THE INVENTION

This invention pertains to apparatus for medical ventilation and, more particularly, to apparatus for controlling the inspiratory and expiratory flow and pressure of gases within a medical ventilator.

Medical ventilators, particularly anesthesia ventilators, generally offer only limited ventilatory modes of operation to the treating physician or anesthesiologist. These ventilators often comprise a flow-control valve for controlling inspiratory flow and adjustable mechanical means, if any, for controlling expiratory flow. Such mechanical means, however, are difficult to monitor and provide little flexibility. Medical ventilators offering more comprehensive ventilatory options generally are not available in anesthesia ventilators and, moreover, require complicated pneumatic hardware. This requirement increases the expense of manufacturing and requires independent control of several pneumatic valves and circuits.

SUMMARY OF THE INVENTION

The present invention provides apparatus for controlling both the flow and pressure of gases in a medical ventilator, throughout the respiratory cycle, using a single inspiratory flow-control valve. This valve provides complete control of pressure or flow at any point within the pneumatic circuit during both inspiration and expiration. Appropriate feedback signals preferably are provided to the valve's controller to provide inspiratory closed-loop flow control and continuous inspiratory and expiratory closed-loop pressure control. The present invention, therefore, provides for an anesthesia ventilator modes of ventilation normally available only in an advanced intensive care unit (ICU) ventilator, such as, e.g., constant positive airway pressure (CPAP), pressure support ventilator (PSV) and adjustable PEEP. Also, by removing the ventilator's bellows assembly and providing inspiratory flow directly to the patient's mouth, the present invention provides an advanced, multi-functional ICU ventilator.

In one aspect, the present invention comprises a first inspiratory conduit for directing a flow of gas from a terminal space, an inspiratory flow-control means for controlling the inspiratory flow of the gas into the terminal space, and an expiratory conduit for directing an expiratory flow of the gas from the terminal space. Means are provided for isolating the expiratory flow from the first inspiratory conduit. Additionally, pressure-control means are provided for causing the gas's pressure within the expiratory flow to track the pressure within the first inspiratory conduit.

The terminal space may comprise, e.g., a bellows assembly or the patient's mouth. In the latter case, the medical ventilator functions as an advanced ICU ventilator, and the gas comprises respiratory gas for the patient's breathing.

The inspiratory flow-control means preferably comprises a proportional solenoid valve, and the means for isolating preferably comprises a second inspiratory conduit and means for prohibiting the gas from flowing from the second inspiratory conduit to the first inspiratory conduit.

The pressure-control means preferably includes a diaphragm or balloon-type valve and means for connecting the first inspiratory conduit to the back chamber of the diaphragm valve. In one embodiment, the connecting means connects the first inspiratory conduit directly to the back chamber of the diaphragm valve and comprises means for releasing the gas to the surrounding atmosphere. In a second embodiment, the connecting means comprises a two-position solenoid valve. In one of the solenoid valve's two positions, the valve provides means for releasing the gas to the surrounding atmosphere and for connecting the first inspiratory conduit to the back chamber of the diaphragm valve. In the other of the solenoid valve's two positions, it provides means for preventing the release of gas to the surrounding atmosphere and for connecting a supply of gas at a predetermined pressure to the back chamber of the diaphragm valve. The connecting means also may comprise means for releasing the gas to an exhaust space having a pressure below that of the surrounding atmosphere.

In a further aspect of the present invention, the medical ventilator comprises processing means and pressure feedback means for detecting the pressure of the gas within the first inspiratory conduit. The pressure feedback means provides a signal indicative of this pressure to the processing means, and the processing means in turn controls the inspiratory flow-control means to cause the pressure within the first inspiratory conduit to track a desired pressure. The feedback means alternatively may be placed within the terminal space or at any other location within the pneumatic circuit.

In another aspect of the present invention, the feedback means may be a flow sensor to detect the inspiratory flow, and the processing means provides means for controlling the inspiratory flow-control means to cause this flow to track a desired flow.

Other objects, features and advantages of the present invention will be more readily apparent from the detailed description of the preferred embodiments set forth below, taken in conjunction with the accompanying drawings.

DESCRIPTION OF THE DRAWINGS

FIG. 2 is a schematic diagram of an alternative embodiment for the connecting valve shown in FIG. 1;

FIG. 3 is a schematic diagram of a second alternative embodiment for the connecting valve shown in FIG. 1;

FIG. 5 is a functional block diagram illustrating use of a medical ventilator in accordance with the present invention as an ICU ventilator.

DETAILED DESCRIPTION OF THE PREFERRED EMBODIMENTS

Figure 1:
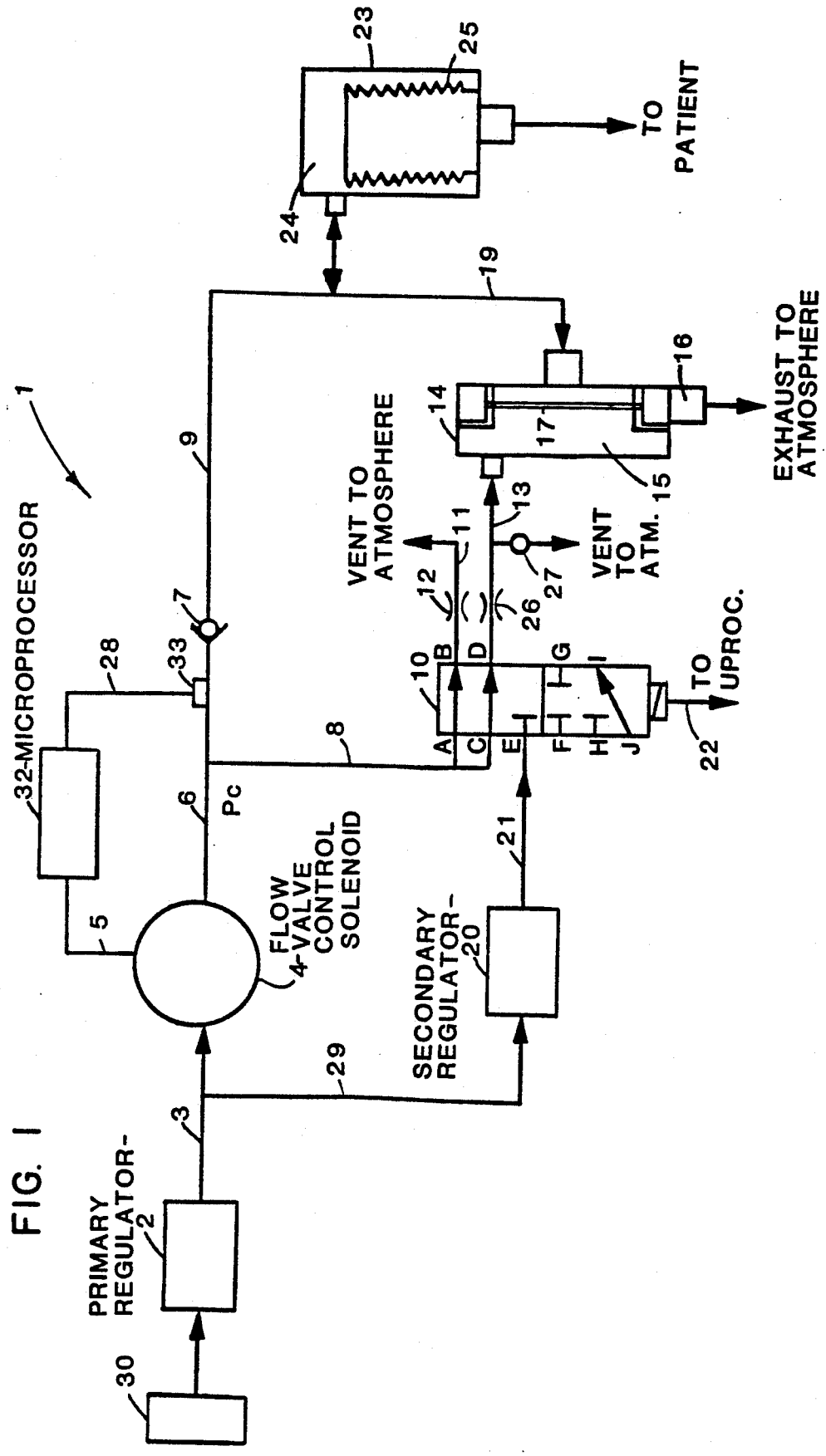
FIG. 1 is a functional block diagram of a medical ventilator in accordance with the present invention.

A medical ventilator 1 in accordance with the present invention is shown in FIG. 1. A source of gas 30 enters medical ventilator 1 through primary regulator 2. Primary regulator 2 maintains this gas at a pressure suitable for use by the ventilator. For example, a source having a pressure of 50 psi is regulated to exit from primary regulator 2 at a pressure of 26 psi. The gas exiting primary regulator 2 enters source conduits 3 and 29.

The gas in source conduit 3 enters flow-control valve 4. This valve controls the magnitude of the flow of gas passing through it, and is itself controlled by microprocessor 32 via signals transmitted on line 5. Microprocessor 32 controls the flow according to a predetermined pressure or flow waveform selected by the operator or technician and provided to the microprocessor by a waveform generator (not shown). The flow-control valve 4 is preferably a high-grade proportional solenoid valve, but single or multiple pulse-width modulated (PWM) two-position valves also may be used.

Gas from flow-control valve 4 enters two conduits, inspiratory conduit 6 and pressure-control conduit 8. Check valve 7, at the end of conduit 6, allows gas to flow into conduit 9 only if the pressure in conduits 6 and 8 is greater than the pressure in conduit 9. If the pressure in conduits 6 and 8 is less than the pressure in conduit 9, on the other hand, check valve 7 closes to prevent the flow of gas from conduit 9 back into conduit 6.

Pressure-control conduit 8 terminates at input ports A and C of connecting valve 10. This valve may be a five-port, two-position solenoid valve, as shown in FIG. 1. In its deactivated position, shown in FIG. 1, pressure-control conduit 8 is connected to input ports A and C, which are, respectively, connected to output ports B and D. Output port B vents to the atmosphere through conduit 11 and pneumatic resistor 12. This resistor has a relatively high pneumatic resistance for reduced gas consumption. Rather than being a fixed resistor, pneumatic resistor 12 may be variable and controlled by microprocessor 32 to optimize performance and gas consumption.

Output port D vents to conduit 13, through pneumatic resistor 26, and into expiratory valve 14, preferably a diaphragm or balloon-type valve. Gas from conduit 13 enters back chamber 15 of expiratory valve 14. If the pressure in back chamber 15 is greater than the pressure in expiratory conduit 19, diaphragm 17 effectively seals the gas present in conduit 19 from flowing through exhaust 16 and into the atmosphere. On the other hand, if the pressure in conduit 19 is greater than the pressure in back chamber 15, diaphragm 17 opens and the gas in conduit 19 flows through expiratory valve 14 and out through exhaust 16.

A safety valve 27 may be disposed on conduit 13. This valve opens when the pressure within this conduit exceeds a predetermined safe level. Safety valve 27 may be located at other places within the pneumatic circuit, such as, e.g., within conduits 6 or 9. Preferably, safety valve 27 opens at a pressure of approximately 1.4 psi.

Connecting valve 10 is moved to its activated position in response to a signal from microprocessor 32 on control line 22. In its activated position, pressure-control conduit 8 is disconnected from ports A and C of connecting valve 10 and is connected to ports F and H, both of which are blocked. Also, in this position, port G, which also is blocked, is connected to conduit 11, and conduit 13 receives gas from sealing conduit 21 across ports J and I. Secondary regulator 20 receives gas from conduit 29, preferably at a pressure of approximately 26 psi, and transmits this gas at a lower pressure, preferably at approximately 1.4 psi, to seal diaphragm 17 during normal operating conditions.

Gas flowing into conduit 9 enters the outer chamber 24 of bellows assembly 23, integrates to pressure, and compresses bellows 25. Gases within these bellows, generally containing anesthetic agents, are transmitted to the patient. By omitting bellows assembly 23 and terminating conduits 9 and 19 directly at the patient's mouth 150, as shown in FIG. 5, however, medical ventilator 1 can function as an ICU respiratory ventilator.

FIGS. 2 and 3 show alternative embodiments for connecting valve 10. As shown in FIG. 2, the five-port, two-position solenoid valve shown in FIG. 1 can be replaced with two solenoid valves in series, namely, one two-port two-position solenoid valve and one four-port two-position solenoid valve. These valves are shown in FIG. 2 in their deactivated positions, with pressure-control conduit 8 connected across ports A and B to conduit 11, and across ports C and D to conduit 13. In their activated position, conduit 21 is connected across ports J and I to conduit 13, and pressure-control conduit 8 is sealed by ports F and H.

FIG. 3 shows another embodiment for connecting valve 10. In this embodiment, three two-port, two-position solenoid valves are connected in series. These valves are shown in their deactivated positions, with pressure-control conduit 8 connected across ports A and B to conduit 11, and across ports C and D to conduit 13. In the activated position, conduit 21 is connected across ports J and I to conduit 13, and pressure-control conduit 8 is sealed by ports F and H.

Microprocessor 32 can control the pressure within outer chamber 24 of bellows assembly 23 during both inspiratory and expiratory flow solely by controlling flow-control valve 4. In this pressure-control mode, connecting valve 10 remains in the deactivated position shown in FIG. 1 during both inspiratory and expiratory flow. To increase the pressure of gas within outer chamber 24, microprocessor 32 commands flow-control valve 4 to increase the flow of gas from source conduit 3 into conduits 6 and 8. The introduction of additional gas into conduits 6 and 8 eventually results in the pressure within these conduits exceeding the pressure within conduits 9 and 19 and outer chamber 24. Upon this occurrence, check valve 7 opens and gas flows from conduit 6, through conduit 9 and into outer chamber 24. This gas compresses bellows 25 and causes gas within these bellows to enter the patient.

Since connecting valve 10 is deactivated, pressure-control conduit 8 is in pneumatic communication with back chamber 15 through ports C and D of connecting valve 10 and conduit 13. The pressure of gas within back chamber 15 of expiratory valve 14, therefore, continuously tracks the pressure of gas within conduits 6 and 8. As a result, when check valve 7 opens, diaphragm 17 closes because the pressure within back chamber 15 (equal to that within conduit 6 and 8) exceeds the pressure within expiratory conduit 19 (equal to that within conduits 9 and outer chamber 24).

When check valve 7 opens, most of the gas flowing from flow-control valve 4 enters outer chamber 24. A portion of this gas, however, is vented to the atmosphere through ports A an B, and conduit 11, but this loss is small because the pneumatic resistance of pneumatic resistor 12 is high. In order to further diminish this loss, however, connecting valve 10 may be activated during all, or during a portion of, the period of flow into outer chamber 24

To decrease the pressure within outer chamber 24, microprocessor 32 commands flow-control valve 4 to reduce the flow of gas from source conduit 3 into conduits 6 and 9. Eventually, this reduced flow causes the pressure within conduits 6 and 8 to drop below that within conduits 9 and 19, and check valve 7 closes. Again, since the pressure within back chamber 15 tracks that within conduits 6 and 8, diaphragm 17 opens when this valve closes. The opening of diaphragm 17 enables an expiratory flow of gas from outer chamber 24 to the atmosphere through expiratory conduit 19 and exhaust 16.

Medical ventilator 1 can control the pressure of this expiratory flow through flow-control valve 4. During expiration, gas within conduits 6 and 8 vents to the atmosphere through ports A and B of connecting valve 10, pneumatic resistor 12 and conduit 11. If the flow through flow-control valve 4 is increased to increase this venting, the pressure within conduits 6 and 8 also increases. Since the pressure within back chamber 15 tracks that within conduits 6 and 8, this increased pressure is transmitted to the expiratory flow of gas from expiratory conduit 19 and outer chamber 24. This transmission occurs because the increased pressure within back chamber 15 reduces the opening of diaphragm 17 and, therefore, increases the pressure within the gas flowing from expiratory conduit 19.

The expiration of gas from outer chamber 24 eventually causes the pressure within this chamber, and within conduits 9 and 19, to fall below that within conduits 6, 8, 13 and back chamber 15. Upon this occurrence, expiratory valve 14 again closes and check valve 7 again opens to cause a renewed inspiratory flow, controlled by flow-control valve 4, into outer chamber 24.

Through control of only flow-control valve 4, therefore, medical ventilator 1 controls the pressure within the inspiratory flow into, and the expiratory flow from, outer chamber 24 of bellows assembly 23. This control provides the anesthesia ventilator with a wide range of ventilatory-mode options such as, e.g., adjustable positive expiratory end pressure (PEEP). Also, as indicated above, by deleting bellows assembly 23 and terminating inspiratory conduit 9 and expiratory conduit 19 directly at the patient's mouth 150, as shown in FIG. 5, medical ventilator 1 provides a multi-functional ICU ventilator capable of providing all known (and unknown) ventilatory modes through control of only flow-control valve 4. A hospital, therefore, can use medical ventilator 1 as both an anesthesia ventilator and an ICU ventilator.

By providing pressure-feedback signals to microprocessor 32 from any point within the pneumatic circuit, such as, e.g., from inspiratory conduit 6 via sensor 33, flow-control valve 4 can be controlled by microprocessor 32 to control pressure within the pneumatic circuit in a closed-loop fashion. In accordance with such control, microprocessor 32 responds to the actual pressure measured by sensor 33 (Pc) with commands to flow-control valve 4 to reduce the magnitude of any deviation between this actual pressure and a desired pressure. A waveform generator (not shown) provides a signal to microprocessor 32 indicative of this desired pressure.

For closed-loop pressure-control, connecting valve 10 again remains in its deactivated position (as shown in FIG. 1). If at any given instant of time (clock cycle), the actual pressure (Pc) sensed by sensor 33 is less than the desired pressure indicated by the desired pressure waveform, microprocessor 32 responds by commanding an increased flow of gas from flow-control valve 4. This increased flow raises the pressure within conduits 6 and 8 and, therefore, decreases the magnitude of this differential. Also, if during this particular instant of time check valve 7 is open and expiratory valve 14 is closed (i.e., Pc is greater than the pressure within conduits 9 and 19 and outer chamber 24), this increased pressure is transmitted to outer chamber 24 through an inspiratory flow into this chamber from conduits 6 and 9. On the other hand, if during this particular instant of time, check valve 7 is closed and expiratory valve 14 is open (i.e., Pc is less than the pressure within conduits 9 and 19 and outer chamber 24), then this increased pressure is transmitted through the expiratory flow from this chamber through conduit 19 and expiratory valve 14. This transmission occurs via pressure-control conduit 8, ports C and D of connecting valve 10 and conduit 13 to back chamber 15 of expiratory valve 14. The increased pressure in conduit 8, of course, also results in an increased flow to the atmosphere through ports A and B of connecting valve 10, pneumatic resistor 12 and conduit 11. As explained above, the increased pressure within back chamber 15 decreases the extent to which expiratory valve 14 is open and, therefore, increases the pressure within the expiratory flow from outer chamber 24.

On the other hand, if the actual pressure (Pc) sensed by sensor 33 is greater than the desired pressure indicated by the desired pressure waveform, microprocessor 32 responds by commanding a reduced flow from flow-control valve 4. In a manner analogous to increasing the flow through this valve, the resultant decreased pressure within conduits 6 and 8 is transmitted to outer chamber 24 via conduit 9, if an inspiratory flow is occurring into this chamber, or via back chamber 15 and expiratory conduit 19, if an expiratory flow is occurring from this chamber. By controlling only flow-control valve 4, therefore, the pneumatic circuit of medical ventilator 1 enables continuous closed-loop pressure-control throughout the respiratory cycle, i.e., during both inspiratory flow into, and expiratory flow from, bellows assembly 23 (or the patient's mouth 150).

Also, continuous closed-loop pressure control can be provided regardless of the location of sensor 33. Sensor 33 can be located, e.g., within conduits 9 or 19, outer chamber 24 or within the patient's mouth 150 or other respiratory organs. Since a treating physician or anesthesiologist often is most concerned with the actual pressures existing within the patient's respiratory organs, such a location is particularly advantageous for sensor 33 (regardless of the presence or absence of bellows assembly 23).

The provision of continuous closed-loop control also is advantageous if a spontaneous breath or cough occurs at any point during the pressure cycles commanded by the desired pressure waveform. For example, if a spontaneous breath occurs during expiratory flow from outer chamber 24, a pressure differential immediately occurs between conduits 6 and 9 causing check valve 7 to open. The opening of this valve causes a flow of gas into outer chamber 24 to support this breath. This action also causes a drop in the magnitude of Pc which causes microprocessor 32 to command an increased flow from flow-control valve 4. This increased flow further supports the spontaneous breath and, moreover, raises the pressure within back chamber 15 back to the target pressure indicated by the desired pressure waveform. Eventually, the pressure within outer chamber 24 is raised back to the desired pressure, check valve 7 closes, and expiratory flow resumes at the desired pressure, again controlled by expiratory valve 14.

A patient's cough during inspiratory flow is facilitated in an analogous manner. The resultant increased pressure within outer chamber 24 closes check valve 7 and opens expiratory valve 14 to release this pressure. Concurrently with this action, the raised pressure within conduits 6 and 8 causes microprocessor 32 to reduce the flow from flow-control valve 4. This reduced flow causes a further pressure drop within back chamber 15 to further support the release of pressure from outer chamber 24. Eventually, Pc drops to the desired pressure, expiratory valve 14 closes, check valve 7 reopens and inspiratory flow resumes at the desired pressure. In this manner, therefore, spontaneous inhalations and exhalations are supported and facilitated, and continuous closed-loop pressure-control is maintained. Also, since the pressure within bellows assembly 23, or equivalently, patient mouth pressure, can be made to follow any target pressure waveform, medical ventilator 1 can function as a high performance ICU ventilator capable of performing constant positive airway pressure (CPAP), pressure support ventilation (PSV), positive end expiratory pressure (PEEP) and other known and unknown ventilatory modes of control.

Medical ventilator 1 also is capable of inspiratory flow-control. In this mode of operation, the volume of gas flowing through conduits 6 and 9 is regulated during inspiration, and connecting valve 10 is switched to its activated position during inspiration. When connecting valve 10 is activated, gas from secondary regulator 20 at approximately 1.4 psi flows through conduit 21, connecting valve 10 (across ports J and I), conduit 13, pneumatic resistor 26, and into back chamber 15 of expiratory valve 14. Back chamber 15 reaches a pressure of approximately 1.4 psi, therefore, which seals diaphragm 17 and expiratory conduit 19 to prevent gas from flowing through this conduit to exhaust 16. Also, pressure-control conduit 8 is closed by input ports F and H of connecting valve 10. All gas from flow-control valve 4, therefore, flows through conduits 6 and 9 and into outer chamber 24, and this flow is controlled by flow-control valve 4 in response to control signals from microprocessor 32 on line 5.

Closed-loop control of this flow may be achieved by transmitting flow-magnitude feedback signals, from sensor 33, to microprocessor 32 on line 28. The microprocessor then controls flow-control valve 4 such that the actual volume of gas flowing through the inspiratory conduits tracks a target waveform, provided to the microprocessor from a target waveform generator (not shown).

In response to a signal from microprocessor 32, connecting valve 10 is switched to the deactivated position, shown in FIG. 1, and the flow from flow-control valve 4 is terminated (or set to provide some positive end back pressure (PEEP) to the back of diaphragm 17). Gas in back chamber 15 vents to the atmosphere through expiratory conduit 13, ports D and C of connecting valve 10, ports A and B of this valve, and finally through conduit 11. The pressure within outer chamber 24 and conduits 9 and 19 eventually exceeds the pressure within conduits 6 and 8 and back chamber 15, and, as a result, check valve 7 closes, diaphragm 17 opens, and gas leaves outer chamber 24 and passes through conduit 19, expiratory valve 14, and out exhaust 16.

Medical ventilator 1 comprises several safety features. For example, in the event of a power shut-down, flow-control valve 4 fails in a zero flow position, and connecting valve 10 fails in the deactivated position shown in FIG. 1. The entire pneumatic circuit, therefore, is vented to the atmosphere.

A more hazardous type of failure occurs if flow-control valve 4 becomes stuck in a wide-open or full-flow position which would drive the pressure in conduit 6 and bellows assembly 25 to a high level. In this event, however, safety valve 27 opens to prevent the pressures within the pneumatic circuit from exceeding a safe level. Preferably, the safety valve is mechanical, and is triggered by pressures greater than 1.4 psi. Once safety valve 27 is activated, flow from flow-control valve 4 vents through pressure-control conduit 8, across ports C and D of connecting valve 10, and out safety valve 27 to the atmosphere. This flow also produces a negative pressure difference between the pressure in back chamber 15 of expiratory valve 14 and conduit 19. This differential allows diaphragm 17 to open, and further exhausts the flow in conduit 19 to the atmosphere. Safety valve 27 may be located at other points within the pneumatic circuit, such as, e.g., within conduits 6 or 9.

In another embodiment of the present invention, conduit 11 is vented to a sub-atmospheric pressure to provide a negative pressure bias for expiratory valve 14. This venting can be effected by, e.g., connecting conduit 11 to a venturi (not shown). Since a negative pressure in conduit 11 is transferred to back chamber 15 of expiratory valve 14, the expiratory valve's response time would be improved by such venting and its resistance lowered, especially at low PEEP levels. Also, the existence of a negative pressure would further tend to open expiratory valve 14 in the event of a failure by flow-control valve 4. This improved performance, however, would be traded off against the cost of increased components and additional gas consumption.

Figure 4:
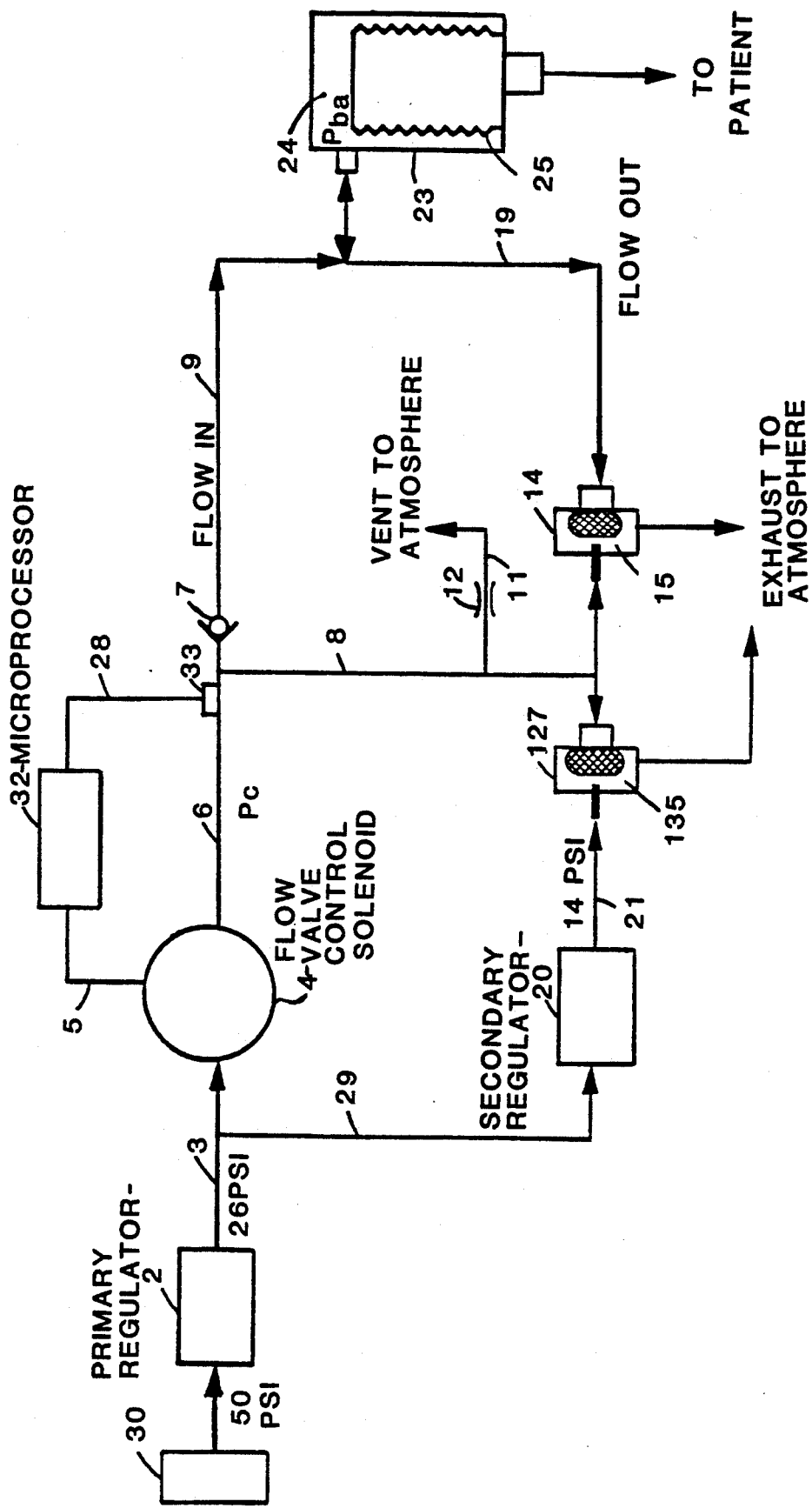
FIG. 4 is a functional block diagram of a second embodiment of a medical ventilator in accordance with the present invention.

FIG. 4 shows another embodiment of the present invention with similar elements similarly numbered. In this embodiment, connecting valve 10, pneumatic resistor 26, and safety valve 27 have been deleted, and pressure-control conduit 8 is connected directly to conduit 11 and back chamber 15 of expiratory valve 14. Also, a diaphragm or balloon-type valve, safety valve 127, has been added which has a continuous pressure, preferably 1.4 psi, applied to its back chamber 135 from secondary regulator 20.

The embodiment shown in FIG. 4 regulates the pressure of gas flowing into, and out of, bellows assembly 23, in either an open or closed-loop fashion, in the same manner as the embodiment shown in FIG. 1. An overpressure condition is prevented, however, by secondary regulator 20 and safety valve 127. If the pressure in pressure-control conduit 8 is driven above 1.4 psi, safety valve 127 opens to vent gas to the atmosphere. This venting also produces a negative pressure difference between the pressure in back chamber 15 and that in conduit 19, allowing expiratory valve 14 to open and exhausting gas in conduit 19 to the atmosphere.

The embodiment shown in FIG. 4 also can operate in a flow-control mode by calculating, and providing to microprocessor 32, the pressure and flow characteristics of pneumatic resistor 12. Since the instantaneous pressure within conduit 8 is known to the microprocessor (via signals from sensor 33), microprocessor 32 can calculate for any given instant of time the volume of gas flowing into the atmosphere through conduit 11. By deducting this flow from the total flow through flow-control valve 4 and conduit 6, the total inspiratory flow through conduit 9 and into bellows assembly 23 can be controlled.

As with the previous embodiments, the bellows assembly may be omitted from the embodiment shown in FIG. 4 and inspiratory gas transmitted directly to the patient's mouth 150, as shown in FIG. 5.

Although particular embodiments of the present invention have been shown and described, many varied embodiments incorporating the teachings of the present invention may be easily constructed by those skilled in the art. The foregoing description of the preferred embodiments, therefore, should be taken as illustrating, rather than limiting, the invention as defined in the following claims.

We claim:

1. A medical ventilator for providing anesthesia to a patient, comprising:
   (a) a first inspiratory conduit;
   (b) inspiratory flow-control means for controlling an inspiratory flow of gas within said first inspiratory conduit;
   (c) a second inspiratory conduit, in communication with said first inspiratory conduit, such that said inspiratory flow travels from said first inspiratory conduit into said second inspiratory conduit;
   (d) a bellows assembly, in communication with said second inspiratory conduit, such that said inspiratory flow travels from said second inspiratory conduit into said bellows assembly;
   (e) an expiratory conduit, in communication with said bellows assembly, such that an expiratory flow of gas travels from said bellows assembly into said expiratory conduit;
   (f) means for preventing said expiratory flow from traveling into said first inspiratory conduit; and
   (g) pressure-control means for causing the pressure of gas comprising said expiratory flow to vary concomitantly with variations in the pressure of the gas within said first inspiratory conduit.

2. A medical ventilator as in claim 1, wherein said pressure-control means comprises a diaphragm valve having a back chamber and means for connecting said first inspiratory conduit to said back chamber of said diaphragm valve.

3. A medical ventilator as in claim 2, wherein said means for connecting comprises a conduit having means for releasing gas to the surrounding atmosphere and wherein said means for preventing comprises a one-way check valve connecting said first inspiratory conduit to said second inspiratory conduit.

4. A medical ventilator as in claim 1, further comprising pressure-feedback means for detecting the pressure of gas within said first inspiratory conduit and for providing a signal indicative of said pressure, and processing means for receiving said signal and for controlling said inspiratory flow-control means to cause said pressure within said first inspiratory conduit to track a desired pressure.

5. A medical ventilator as in claim 1, further comprising pressure-feedback means for detecting the pressure of gas within said bellows assembly and for providing a signal indicative of said pressure, and processing means for receiving said signal and for controlling said inspiratory flow-control means to cause said pressure within said bellows assembly to track a desired pressure.

6. A medical ventilator as in claim 1, further comprising pressure-feedback means for detecting the pressure of gas within said patient's mouth and for providing a signal indicative of said pressure, and processing means for receiving said signal and for controlling said inspiratory flow-control means to cause said pressure within said patient's mouth to track a desired pressure.

7. A medical ventilator as in claim 1, further comprising flow-sensor means for detecting the magnitude of said inspiratory flow and for providing a signal indicative of said magnitude, and processing means for receiving said signal and for controlling said inspiratory flow-control means to cause said magnitude to track a desired magnitude.

* * * * *